US006692957B2

(12) United States Patent
Goldman et al.

(10) Patent No.: US 6,692,957 B2
(45) Date of Patent: *Feb. 17, 2004

(54) METHOD FOR SEPARATING CELLS

(75) Inventors: Steven A. Goldman, South Salem, NY (US); Hong Wu, New York, NY (US)

(73) Assignee: Cornell Research Foundation, Inc., Ithaca, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/836,570

(22) Filed: Apr. 17, 2001

(65) Prior Publication Data

US 2002/0061586 A1 May 23, 2002

Related U.S. Application Data

(63) Continuation of application No. 08/787,788, filed on Jan. 23, 1997, now Pat. No. 6,245,564.

(51) Int. Cl.$^7$ .............................. C12N 5/02; C12N 5/08
(52) U.S. Cl. ....................... 435/368; 435/366; 435/325; 435/377
(58) Field of Search ................................ 435/366, 368, 435/354, 325, 1.1, 404, 377

(56) References Cited

U.S. PATENT DOCUMENTS

| | | | |
|---|---|---|---|
| 4,997,929 | A | 3/1991 | Collins et al. |
| 5,082,774 | A | 1/1992 | Heinrich |
| 5,145,774 | A | 9/1992 | Tarnowski et al. |
| 5,169,762 | A | 12/1992 | Gray et al. |
| 5,196,315 | A | 3/1993 | Ronnett et al. |
| 5,217,893 | A | 6/1993 | Ronnett et al. |
| 5,272,063 | A | 12/1993 | Chan et al. |
| 5,308,763 | A | 5/1994 | Ronnett et al. |
| 5,338,839 | A | 8/1994 | McKay et al. |
| 5,491,084 | A | 2/1996 | Chalfie et al. |
| 5,502,176 | A | 3/1996 | Tenen et al. |
| 5,753,506 | A | 5/1998 | Johe |
| 5,874,304 | A | 2/1999 | Zolotukhin et al. |
| 6,146,826 | A * | 11/2000 | Chalfie et al. |
| 6,146,888 | A | 11/2000 | Smith et al. |
| 6,150,169 | A | 11/2000 | Smith et al. |

FOREIGN PATENT DOCUMENTS

| | | | |
|---|---|---|---|
| EP | | 0 695 351 B1 | 8/1999 |
| WO | | WO 96/38541 | 12/1996 |
| WO | | WO 97/07200 | 2/1997 |
| WO | | WO 99/29279 | 6/1999 |

OTHER PUBLICATIONS

Gloster et al., "The T alpha 1 alpha–tubulin Promoter Specifies Gene Expression as a Function of Neuronal Growth and Regeneration in Transgenic Mice," *J. Neurosci.* 14(12):7319–30 (1994).

Angelichio et al., "Comparison of Several Promoters and Polyadenylation Signals for Use in Heterologous Gene Expression in Cultured Drosophila Cells," *Nuc. Acids Res.* 19(18):5037–43 (1991).

Schatz et al., "Isolation and Characterization of Conditional–lethal Mutations in the TUB1 alpha–tubulin Gene of the Yeast *Saccharomyces cerevisiae*," *Genetics* 120(3):681–95 (1988).

Schatz et al., "Insertions of up to 17 Amino Acids into a Region of alpha–tubulin Do Not Disrupt Function In Vivo," *Mol. Cell Biol.* 7(10):3799–805 (1987).

Schatz et al., "Genetically Essential and Nonessential alpha–tubulin Genes Specify Functionally Interchangeable Proteins," *Mol. Cell Biol.* 6(11):3722–33 (1986).

Schatz et al., "Two Functional alpha–tubulin Genes of the Yeast *Saccharomyces cerevisiae* Encode Divergent Proteins," *Mol. Cell Biol.* 6(11):3711–21 (1986) (abstract).

Largent et al., "Directed Expression of an Oncogene to the Olfactory Neuronal Lineage in Transgenic Mice," *J. Neuroscience* 13(1):300–312 (1993).

Doevendans et al., "The Utility of Fluorescent In vivo Reporter Genes in Molecular Cardiology," *Biochem. and Biophys. Res.* 222:352–358 (1996).

Prasher, "Using GFP to See the Light," *Trends in Genetics* 11(8):320–323 (1995).

\* cited by examiner

*Primary Examiner*—Marianne P. Allen
(74) *Attorney, Agent, or Firm*—Nixon Peabody LLP (57) ABSTRACT

The present invention is directed to a method of separating cells of interest which method comprises: determining cells of interest; selecting a promoter specific for the cells of interest; introducing a nucleic acid molecule encoding green fluorescent protein under control of the promoter into a plurality of cells; and separating cells of the plurality of cells that are expressing said green fluorescent protein, wherein the separated cells are the cells of interest.

28 Claims, 6 Drawing Sheets

SEQUENCE LISTING

<160> NUMBER OF SEQ ID NOS: 2

<210> SEQ ID NO 1
<211> LENGTH: 26
<212> TYPE: DNA
<213> ORGANISM: Artificial Sequence
<220> FEATURE:

-continued

```
<223> OTHER INFORMATION: Description of Artificial Sequence:  primer

<400> SEQUENCE: 1
cttacatatg ctgaattccg tattag                                      26

<210> SEQ ID NO 2
<211> LENGTH: 24
<212> TYPE: DNA
<213> ORGANISM: Artificial Sequence
<220> FEATURE:
<223> OTHER INFORMATION: Description of Artificial Sequence:  primer

<400> SEQUENCE: 2
gctcaccggt gttgctgctt cgcg                                        24
```

METHOD FOR SEPARATING CELLS

The present application is a continuation of U.S. patent application Ser. No. 08/787,788, filed Jan. 23, 1997, now U.S. Pat. No. 6,245,564.

The subject matter of this application was made with support from the United States Government under grants RO1 NS33106, R29 NS29813 and 5T32 NSO7141-17 of the National Institutes of Health.

FIELD OF THE INVENTION

The present invention relates generally to a method of separating cells of interest from organs and from larger populations of mixed cell types. In particular, this invention includes the introduction of a nucleic acid molecule encoding a green fluorescent protein, under the control of a cell-specific promoter, into a plurality of cells and then separating the cells of interest by detecting fluorescence in those cells in which the cell-specific promoter drives expression of the green fluorescent protein.

BACKGROUND OF THE INVENTION

Throughout this application various publications are referenced, many in parenthesis. Full citations for these publications are provided at the end of the Detailed Description. The disclosures of these publications in their entireties are hereby incorporated by reference in this application.

The damaged brain is largely incapable of functionally significant structural self-repair. This is due in part to the apparent failure of the mature brain to generate new neurons (Korr, 1980; Sturrock, 1982). However, the absence of neuronal production in the adult vertebrate forebrain appears to reflect not a lack of appropriate neuronal precursors, but rather their tonic inhibition and/or lack of post-mitotic trophic and migratory support. Converging lines of evidence now support the contention that neuronal precursor cells are distributed widely throughout the ventricular subependyma of the adult vertebrate forebrain, persisting across a wide range of species groups (Goldman and Nottebohm, 1983; Reynolds and Weiss, 1992; Richards et al., 1992; Kirschenbaum et al., 1994; Kirschenbaum and Goldman, 1995a; reviewed in Goldman, 1995; Goldman, 1997; and Gage et al., 1995). Most studies have found that the principal source of these precursors is the ventricular zone (Goldman and Nottebohm, 1983; Goldman, 1990; Goldman et al., 1992; Lois and Alvarez-Buylla, 1993; Morshead et al., 1994; Kirschenbaum et al., 1994; Kirschenbaum and Goldman, 1995), though competent neural precursors have been obtained from parenchymal sites as well (Richards et al., 1992; Palmer et al., 1996; Pincus et al., 1996). In general, adult progenitors respond to epidermal growth factor (EGF) and basic fibroblast growth factor (bFGF) with proliferative expansion (Reynolds and Weiss, 1992; Kilpatrick and Bartlett, 1995), may be multipotential (Vescovi et al., 1993; Goldman et al., 1996), and persist throughout life (Goldman et al., 1996). In rodents and humans, their neuronal daughter cells can be supported by brain-derived neurotrophic factor (BDNF) (Kirschenbaum and Goldman, 1995a), and become fully functional in vitro (Kirschenbaum et al., 1994), like their avian counterparts (Goldman and Nedergaard, 1992; Pincus et al., 1996). In general, residual neural precursors are widely distributed geographically, but continue to generate surviving neurons only in selected regions; in most instances, they appear to become vestigial (Morshead and van der Kooy, 1992), at least in part because of the loss of permissive signals for daughter cell migration and survival in the adult parenchymal environment.

A major impediment to both the analysis of the biology of adult neuronal precursors, and to their use in engraftment and transplantation studies, has been their relative scarcity in adult brain tissue, and their consequent low yield when harvested by enzymatic dissociation and purification techniques. As a result, attempts at either manipulating single adult-derived precursors or enriching them for therapeutic replacement have been difficult. The few reported successes at harvesting these cells from dissociates of adult brain, whether using avian (Goldman et al., 1992; 1996c), murine (Reynolds and Weiss, 1992), or human (Kirschenbaum et al., 1994) tissue, have all reported <1% cell survival. Thus, several groups have taken the approach of raising lines derived from single isolated precursors, continuously exposed to mitogens in serum-free suspension culture (Reynolds and Weiss, 1992; Morshead et al., 1994; Palmer et al., 1995). As a result, however, many of the basic studies of differentiation and growth control in the neural precursor population have been based upon small numbers of founder cells, passaged greatly over prolonged periods of time at high split ratios, under constant mitogenic stimulation. The phenotypic potential, transformation state and karyotype of these cells are all uncertain; after repetitive passage, it is unclear whether such precursor lines remain biologically representative of their parental precursors, or instead become transformants with perturbed growth and lineage control.

A strong need therefore exists for a new strategy for isolating and enriching native neuronal precursors and neural stem cells from adult brain tissue. Such isolated, enriched native precursors can be used in engraftment and transplantation, as well as for studies of growth control and functional integration.

SUMMARY OF INVENTION

To this end, the subject invention provides a method of separating cells of interest from a larger, heterogeneous cell population, based upon cell-type-selective expression of cell specific promoters. This method comprises: determining the cells of interest; selecting a promoter specific for the cells of interest; introducing a nucleic acid molecule encoding green fluorescent protein under control of the promoter into a plurality of cells; and separating cells of the plurality of cells that are expressing said green fluorescent protein, wherein the separated cells are the cells of interest.

The cells of interest, in a preferred embodiment of the method of the subject invention, are neuronal cells, and particularly neuronal precursor cells. A promoter is chosen which specifically drives expression in the cells of interest, i.e. the promoter drives expression in neuronal precursor cells but not in other cells of the nervous system. The green fluorescent protein will therefore only be expressed and detectable in cells in which the promoter operates, i.e. those cells for which the promoter is specific.

The method involves the introduction of nucleic acid encoding the green fluorescent protein, under the control of the cell specific promoter, into a plurality of cells. Various methods of introduction known to those of ordinary skill in the art can be utilized, including (but not limited to) viral mediated transformation (e.g. adenovirus mediated transformation), electroporation, biolistic transformation, and liposomal mediated transformation.

After cell specific expression of the green fluorescent protein (GFP), the cells expressing the green fluorescent protein are separated by any appropriate means. For example, the cells can be separated by fluorescence activated cell sorting. The method of the subject invention thus provides for the enrichment and separation of the cells of interest.

A presently preferred embodiment of the method of the subject invention relates to neuronal precursor cells which are widespread in the forebrain ventricular zone (VZ), and which may provide a cellular substrate for brain repair. Contemporary approaches toward the use of neuronal precursor cells have focused upon preparing clonal lines derived from single progenitors. However, such propagated lines can become progressively less representative of their parental precursors with time and passage in vitro. To circumvent these difficulties, the method of the subject invention provides a strategy for the live cell identification, isolation and enrichment of native precursors and their neuronal daughter cells, by fluorescence-activated cell sorting of VZ cells transfected with green fluorescent protein, driven by the neuronal Tα1 tubulin promoter. Using this approach, neural precursors and their young neuronal daughters can be identified and selectively harvested from a wide variety of samples, including embryonic and adult brain of both avian and mammalian origin.

Extension of this approach to include fluorescent transgenes under the control of stage- and phenotype-specific promoters (both of which are intended to be covered by reference to "cell specific" promoters herein) allows even more specific separations to be performed, for example, of both neurons and oligodendrocytes over a range of developmental stages. This strategy may be applied to any tissue of interest for which a cell-specific promoter is available, thereby allowing the identification, isolation and separation of progenitor cells and their products from any tissue for which constituent cells have been assigned phenotype selective promoters. This strategy permits sufficient enrichment for in vivo implantation of the defined and separated progenitor pools, as well as for in vitro analyses of phenotypic specification and growth control.

BRIEF DESCRIPTION OF THE DRAWINGS

These and other features and advantages of this invention will be evident from the following detailed description of preferred embodiments when read in conjunction with the accompanying drawings in which.

DETAILED DESCRIPTION

A plasmid designated pGFP10.1 has been deposited pursuant to, and in satisfaction of, the requirements of the Budapest Treaty on the International Recognition of the Deposit of Microorganisms for the Purposes of Patent Procedure, with the American Type Culture Collection (ATCC), 12301 Parklawn Drive, Rockville, Md. 20852 under ATCC Accession No. 75547 on Sep. 1, 1993. This plasmid is commercially available from the ATCC due to the issuance of U.S. Pat. No. 5,491,084 on Feb. 13, 1996 in which the plasmid is described. This plasmid comprises a cDNA which encodes a green fluorescent protein (GFP) of *Aequorea victoria* as disclosed in U.S. Pat. No. 5,491,084 to Chalfie et al., the contents of which are incorporated herein by reference.

Figure 1:
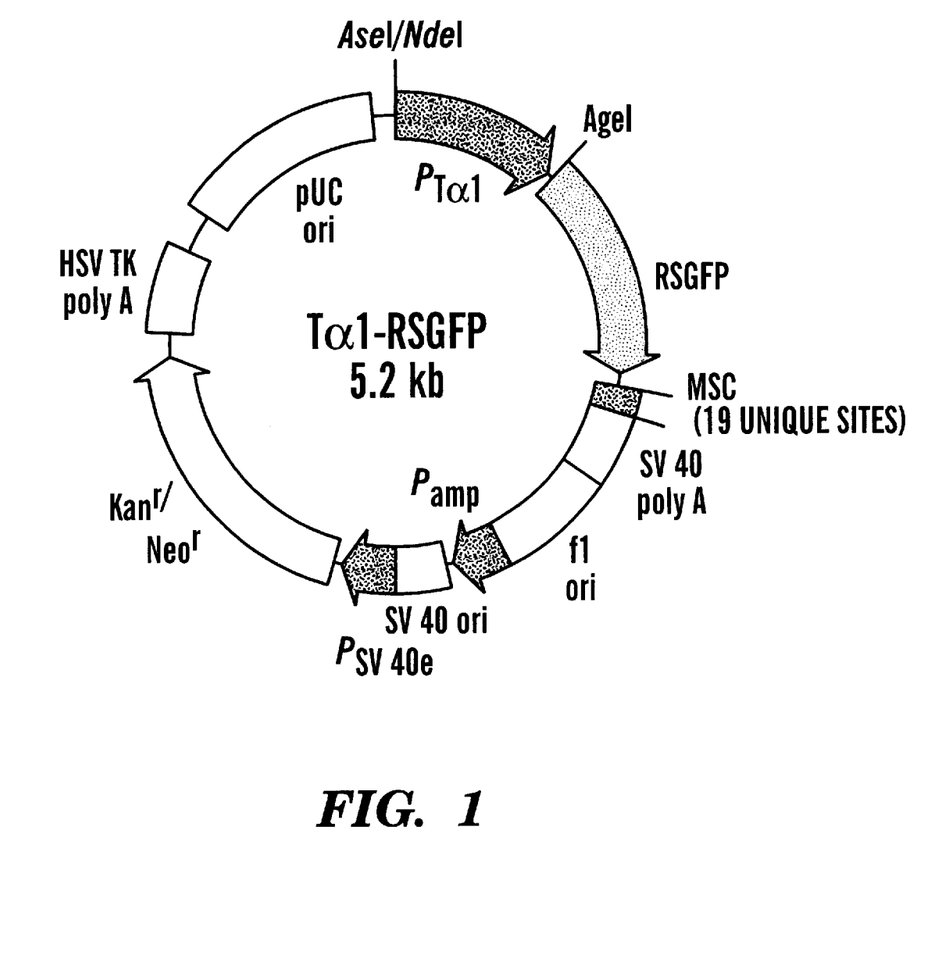
FIG. 1 illustrates the plasmid map of pTα1-RSGFP, using the Tα1 promoter of F. Miller (Montreal) and the RS-GFP of Clontech Laboratories, Inc. (Palo Alto, Calif.). This approach may utilize any form of the GFP expressing sufficient fluorescence to allow epifluorescent detection and fluorescence activated cell sorting (FACS).

The plasmid designated pTα1-RSGFP (FIG. 1) has been deposited pursuant to, and in satisfaction of, the requirements of the Budapest Treaty on the International Recognition of the Deposit of Microorganisms for the Purposes of Patent Procedure, with the American Type Culture Collection (ATCC), 10801 University Blvd.; Manassas Va. 20110-2209 under ATCC Accession No. 98298 on Jan. 21, 1997. This plasmid uses the red shifted GFP (RS-GFP) of Clontech Laboratories, Inc. (Palo Alto, Calif.), and the Tα1 promoter sequence provided by Dr. F. Miller (Montreal Neurological Institute, McGill University, Montreal, Canada). In accordance with the subject invention, the Tα1 promoter can be replaced with another specific promoter, and the RS-GFP gene can be replaced with another form of GFP, by using standard restriction enzymes (see FIG. 1) and ligation procedures.

Figure 7:
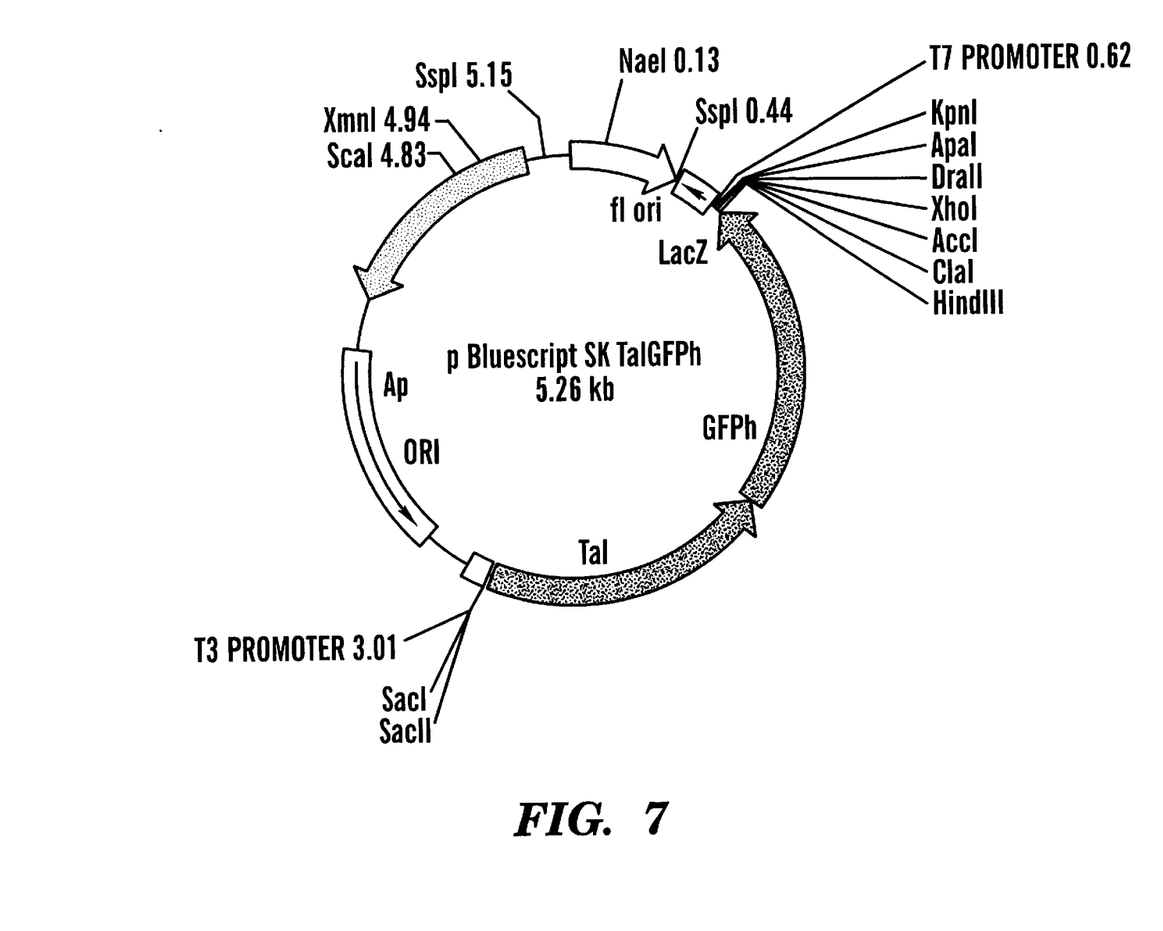
FIG. 7 illustrates the plasmid map of pTα1-GFPh (pBluescript SK Ta1GFPh), using the Tα1 promoter of F. Miller (Montreal) and GFPh of Zolotukhin and Muzyczka (Levy et al. 1996b). This plasmid has the advantage of an additional multiple cloning site proximal to the Tα1 promoter, facilitating replacement of the Tα1 promoter with other promoters. GFPh is used here as a somewhat brighter alternative to RF-GFP, though both are effective for this separation technique. Again, this approach may also utilize any form of the GFP expressing sufficient fluorescence to allow epifluorescent detection and fluorescence activated cell sorting.

The plasmid designated pTα1-GFPh (FIG. 7) has been deposited pursuant to, and in satisfaction of, the requirements of the Budapest Treaty on the International Recognition of the Deposit of Microorganisms for the Purposes of Patent Procedure, with the American Type Culture Collection (ATCC), 10801 University Blvd.; Manassas Va. 20110-2209 under ATCC Accession No. 98299 on Jan. 21, 1997. This plasmid uses the humanized GFP (GFPh) of Zolotukhin and Muzyczka (Levy et al. 1996b), and the Tα1 promoter sequence provided by Dr. F. Miller (Montreal). In accordance with the subject invention, the Tα1 promoter can be replaced with another specific promoter, and the GFPh gene can be replaced with another form of GFP, by using standard restriction enzymes (see FIG. 7) and ligation procedures.

As used herein, the term "isolated" when used in conjunction with a nucleic acid molecule refers to: 1) a nucleic acid molecule which has been separated from an organism in a substantially purified form (i.e. substantially free of other substances originating from that organism), or 2) a nucleic acid molecule having the same nucleotide sequence but not necessarily separated from the organism (i.e. synthesized or recombinantly produced nucleic acid molecules).

The subject invention provides a method of separating cells of interest which method comprises: determining cells of interest; selecting a promoter specific for the cells of interest; introducing a nucleic acid molecule encoding green fluorescent protein under control of the promoter into a plurality of cells; and separating cells of the plurality of cells that are expressing the green fluorescent protein, wherein the separated cells are the cells of interest.

The cells of particular interest according to the subject invention are neuronal cells, more particularly neuronal precursor cells. Any cell which one desires to separate from a plurality of cells can be chosen according to the subject invention, as long as a promoter specific for the chosen cell is available. "Specific", as used herein to describe a promoter, means that the promoter functions only in the chosen cell type. A chosen cell type can refer to different types of cells, or different stages in the developmental cycle of a cell. For example, the chosen cell may be a neuronal precursor cell and the chosen promoter only functions in neuronal precursor cells; i.e. the promoter does not function in adult neuronal cells. Although neuronal precursor cells and adult neuronal cells may both be considered neuronal cells, these cells are different stages of neuronal cells and can be separated according to the subject invention if the chosen promoter is specific to the particular stage of the neuronal cell. The chosen cell may be a neuronal cell, generally, and the chosen promoter only functions in neuronal cells. As another example, the chosen cell may be an oligodendrocyte and the chosen promoter only functions in oligodendrocytes. Those of ordinary skill in the art can readily determine a cell of interest to select based on the availability of a promoter specific for that cell of interest.

Illustrative of possible cell and promoter combinations which can be used in the subject invention are the following: a neuron and a neuron-specific enolase promoter (Andersen et al. 1993; Alouani et al. 1992); a developing or regenerating neuron and a MAP-1B promoter (Liu and Fischer 1996); a neuron and an L1 promoter (Chalepakis et al. 1994); a dopaminergic neuron and an aromatic amino acid decarboxylase promoter (Le Van Thai et al. 1993); a noradrenergic neuron and a dopamine β-hydroxylase promoter (Mercer et al. 1991); a neuron and an NCAM promoter (Holst et al. 1994); a neuronal precursor cell and an NCAM promoter (Holst et al. 1994) ; a neural cell, whether neuronal or oligodendrocytic, and an NCAM promoter (Holst et al. 1994); a neuronal precursor cell and an HES-5 HLH protein promoter (Takebayashi et al. 1995); a neuron and an α1-tubulin promoter (Gloster et al. 1994); a neuronal precursor cell and an α1-tubulin promoter (Gloster et al. 1994); a developing or regenerating neuron and an α1-tubulin promoter (Gloster et al. 1994); a neuron and an α-internexin promoter (Ching et al. 1991); a developing or regenerating neuron and an α-internexin promoter (Ching et al. 1991); a peripheral neuron and a peripherin promoter (Karpov et al. 1992); a mature neuron and a synapsin promoter (Chin et al. 1994); a developing or regenerating neuron and a GAP-43 promoter (Starr et al. 1994); an oligodendrocyte and a cyclic nucleotide phosphorylase I promoter (Scherer et al. 1994); a myelinating oligodendrocyte and a myelin basic protein promoter (Wrabetz et al. 1993); an oligodendrocyte and a JC virus minimal core promoter (Krebs et al. 1995); an oligodendrocyte precursor and a JC virus minimal core promoter (Krebs et al., 1995); a myelinating oligodendrocyte and a proteolipid protein promoter (Cambi and Kamholz 1994); and an oligodendrocyte precursor and a cyclic nucleotide phosphorylase II promoter (Scherer et al. 1994).

Having determined the cell of interest and selected a promoter specific for the cell of interest, a nucleic acid molecule encoding green fluorescent protein under the control of the promoter is introduced into a plurality of cells to be sorted.

The isolated nucleic acid molecule encoding a green fluorescent protein can be deoxyribonucleic acid (DNA) or ribonucleic acid (RNA, including messenger RNA or mRNA), genomic or recombinant, biologically isolated or synthetic. The DNA molecule can be a cDNA molecule, which is a DNA copy of a messenger RNA (mRNA) encoding the GFP. In one embodiment, the GFP can be from Aequorea victoria (Prasher et al., 1992; U.S. Pat. No. 5,491,084;). A plasmid encoding the GFP of Aequorea victoria is available from the ATCC as Accession No. 75547. A mutated form of this GFP (a red-shifted mutant form) designated pRSGFP-C1 is commercially available from Clontech Laboratories, Inc. (Palo Alto, Calif.).

Mutated forms of GFP that emit more strongly than the native protein, as well as forms of GFP amenable to stable translation in higher vertebrates, are now available and can be used for the same purpose. The plasmid designated pTα1-GFPh (ATCC Accession No. 98299) includes a humanized form of GFP. Indeed, any nucleic acid molecule encoding a fluorescent form of GFP can be used in accordance with the subject invention.

Standard techniques are then used to place the nucleic acid molecule encoding GFP under the control of the chosen cell specific promoter. Generally, this involves the use of restriction enzymes and ligation (see below).

The resulting construct, which comprises the nucleic acid molecule encoding the GFP under the control of the selected promoter (itself a nucleic acid molecule) (with other suitable regulatory elements if desired), is then introduced into a plurality of cells which are to be sorted. Techniques for introducing the nucleic acid molecules of the construct into the plurality of cells may involve the use of expression vectors which comprise the nucleic acid molecules. These expression vectors (such as plasmids and viruses) can then be used to introduce the nucleic acid molecules into the plurality of cells.

Various methods are known in the art for introducing nucleic acid molecules into host cells. These include: 1) microinjection, in which DNA is injected directly into the nucleus of cells through fine glass needles; 2) dextran incubation, in which DNA is incubated with an inert carbohydrate polymer (dextran) to which a positively charged chemical group (DEAE, for diethylaminoethyl) has been coupled. The DNA sticks to the DEAE-dextran via its negatively charged phosphate groups. These large DNA-containing particles stick in turn to the surfaces of cells, which are thought to take them in by a process known as endocytosis. Some of the DNA evades destruction in the cytoplasm of the cell and escapes to the nucleus, where it can be transcribed into RNA like any other gene in the cell; 3) calcium phosphate coprecipitation, in which cells efficiently take in DNA in the form of a precipitate with calcium phosphate; 4) electroporation, in which cells are placed in a solution containing DNA and subjected to a brief electrical pulse that causes holes to open transiently in their membranes-DNA enters through the holes directly into the cytoplasm, bypassing the endocytotic vesicles through which they pass in the DEAE-dextran and calcium phosphate procedures (passage through these vesicles may sometimes destroy or damage DNA); 5) liposomal mediated transformation, in which DNA is incorporated into artificial lipid vesicles, liposomes, which fuse with the cell membrane, delivering their contents directly into the cytoplasm; 6) biolistic transformation, in which DNA is absorbed to the surface of gold particles and fired into cells under high pressure using a ballistic device; and 7) viral-mediated transformation, in which nucleic acid molecules are introduced into cells using viral vectors. Since viral growth depends on the ability to get the viral genome into cells, viruses have devised efficient methods for doing so. These viruses include retroviruses and lentivirus, adenovirus, herpesvirus, and adeno-associated virus.

As indicated, some of these methods of transforming a cell require the use of an intermediate plasmid vector. U.S. Pat. No. 4,237,224 to Cohen and Boyer describes the production of expression systems in the form of recombinant plasmids using restriction enzyme cleavage and ligation with DNA ligase. These recombinant plasmids are then introduced by means of transformation and replicated in unicellular cultures including procaryotic organisms and eucaryotic cells grown in tissue culture. The DNA sequences are cloned into the plasmid vector using standard cloning procedures known in the art, as described by Sambrook et al. (1989).

In accordance with one of the above-described methods, the nucleic acid molecule encoding the GFP is thus introduced into a plurality of cells. The promoter which controls expression of the GFP, however, only functions in the cell of interest. Therefore, the GFP is only expressed in the cell of interest. Since GFP is a fluorescent protein, the cells of interest can therefore be identified from among the plurality of cells by the fluorescence of the GFP.

Any suitable means of detecting the fluorescent cells can be used. The cells may be identified using epifluorescence optics, and can be physically picked up and brought together by Laser Tweezers (Cell Robotics Inc., Albuquerque, N.Mex.). They can be separated in bulk through fluorescence activated cell sorting, a method that effectively separates the fluorescent cells from the non-fluorescent cells.

The method of the subject invention thus provides for the isolation and enrichment of neural precursors from embryonic and adult brain of both avian and rodent derivation. Specifically, fluorescence-activated cell sorting of subependymal cells transfected with green fluorescent protein driven by the neuronal Tα1 tubulin promoter is provided. Tα1, a member of the α-tubulin multigene family, is localized almost exclusively to the nervous system, within which it appears specific for neurons (Miller et al., 1987, 1989; Gloster et al., 1994). Though most abundant in young neurons extending neurites, it is first expressed earlier in neuronal ontogeny, including in VZ cells (Miller et al., 1987). The 1.1 kb 5' flanking region from the Tα1 gene contains those sequence elements responsible for specifying Tα1 expression to embryonic neurons, and for regulating its expression as a function of growth (Gloster et al., 1994). Transgenic mice with the 1.1 kb 5' flanking region fused to a nuclear lacZ reporter manifested expression of the Tα1 promoter-driven transgene only within the developing central nervous system, and then only in neurons and the neural VZ, suggesting that Tα1 tubulin promoter was expressed by premitotic VZ precursor cells, as well as their young neuronal progeny (Gloster et al., 1994).

The neuronal specificity and early expression of the Tα1 promoter was capitalized on to use it as a marker for new neurons and their parental precursors. This was done by coupling the Tα1 promoter to the red-shifted mutant form of green fluorescent protein (Chalfie et al., 1994; Heim and Tsien, 1996), and transfecting both embryonic and adult forebrain VZ cells with the resulting construct. These cells were successfully transfected with biolistic particle delivery (using a Bio-Rad PDS 1000), Lipofectin (Life Technologies, Grand Island, N.Y.), and an adenoviral vector bearing GFP (Dr. R. Crystal, Cornell University Medical College, New York, N.Y.); the latter two techniques are particularly appropriate for transfecting Tα1 :GFP into large, mixed cell populations.

Two days after transfection, Tα1 expressing VZ cells, largely either young neurons or their neuronally-specified progenitors, were then identified on the basis of their GFP fluorescence to blue excitation. This approach allowed for the identification and observation, alive and in real time, of VZ precursor cells and their neuronal daughters, derived from both fetal and adult brain. The brilliant fluorescence of these Tα1-driven GFP$^+$ precursor cells permitted their isolation and selective enrichment by fluorescence activated cell sorting (FACS), which yielded cell populations highly enriched in young neurons and their precursors; of the latter, many proceeded to differentiate as neurons in the days following their preparation.

MATERIALS AND METHODS

Embryonic Brain Culture

Embryonic rat and chicken forebrain cultures were prepared as previously described (Goldman et al., 1989; Nedergaard et al., 1991). Briefly, for rat forebrain cultures, pregnant Sprague-Dawley females were sacrificed at 10 days gestation by pentobarbital overdose, and their fetuses removed, decapitated, and their brains dissected free of meningeal tissue and skull osteoid. Similarly, for chick brain cultures, the telencephalic vesicles/forebrain anlagen were dissected from freshly decapitated embryos after 6, 8 or 10 days gestational age. In each case, the samples were immersed in Ca/Mg-free HBSS (10:1, v/v), mixed 1:1 v/v with 0.25% trypsin/1 mM EDTA, then incubated for 15 minutes at 37° C, with intermittent trituration every 5 minutes by repetitive (×10) passage through a fire-polished 9 inch Pasteur pipette. Trypsinization was halted with 1 mg/10 ml soybean trypsin inhibitor, followed by 1:1 mixture in serum-containing culture media. The samples were then spun for 10 minutes at approximately 1000 rpm in an IEC clinical centrifuge, and the resultant pellets resuspended at $5 \times 10^5$ cells/ml in culture medium. The resultant cell suspensions were then plated at 1 ml/dish into 35 mm Falcon Primaria plates coated with murine laminin (1–2 $\mu g/cm^2$), and incubated for 12 hours at 37° C. in 5% $CO_2$/95% air, preceding transfection.

Adult VZ Cell Culture

Culture preparation. Adult rat forebrain vz was cultured as small explants in microcarrier-borne suspension culture, so as to maximize the surface area of tissue presented to the medium, and hence optimize the access of plasmid DNA to individual precursor cells, while avoiding enzymatic dissociation and frank tissue disruption. Adult (300–350 g) Sprague-Dawley rats were sacrificed, and their rostral telencephalic VZ taken from the level of the anterior commisure rostrally to the olfactory subependyma, as previously described (Kirschenbaum and Goldman, 1995). The VZ samples were dissected out manually into sterile HBSS, then cut to 200 $\mu m$ on each side using a McIlwain tissue chopper (Brinkmann).

Microcarrier suspension culture of adult VZ cells. Fragments of adult VZ were resuspended in medium, and mixed 1:1 v/v with a suspension of charged cellulose microcarriers in HBSS (DE53, Whatman; 40×80–400 $\mu m$), as previously described (Shahar, 1990). While incubating 5 min at room temperature, the carrier-borne explants were allowed to settle under gentle centrifugation, and then resuspended in 2.4 ml medium (DMEM/F12/N2 with non-essential amino acids and 50 U/ml penicillin and streptomycin; Goldman et al., 1992), supplemented with 5% fetal bovine serum and 20 ng/ml basic FGF (UBI). Aliquots of 0.6 ml of the resultant suspension, each containing approximately 40 explant fragments, were then distributed to each of 4 petri dishes (35 mm, Falcon), and incubated overnight at 37° C. in a 5% $CO_2$/95% air environment.

Transfection Techniques

1. Liposomal transfection. Embryonic and adult brain cells, the latter derived from dissociates of the forebrain ventricular zone and the former from dissociates of whole forebrain vesicles, were plated as high density slurries, 8–12 hrs before liposomal transfection with pTα1-RSGFP, pCMV-RSGFP-C1 and/or pTα1:lacZ. Each dish received 0.75 μg of DNA and 5 ml of lipofectin (GIBCO), and the cells were incubated with the mixture of DNA-lipid in OPT-medium for 5–7 hrs, then returned to normal media. Imaging for green fluorescence protein expression was performed 12–48 hrs after transfection, using an Olympus IX70 microscope with epifluorescence optics.

2. Particle-mediated gene transfer. An alternative method was also utilized for gene transfer to adult cells, that of particle-mediated delivery, using the Biolistic particle delivery system (Bio-Rad PDS 1000). For this purpose, carrier-bound explant (roughly 100/ml) were plated onto laminin coated 35 mm Falcon dishes, at 0.5 ml/dish. These began to attach almost immediately, and Biolistic transfection was performed 6 hrs thereafter.

For the transfection, gold particles (0.6 or 1 micron, 50 μl of 60 mg/ml, Bio-Rad) were coated with 5 μg plasmid DNA, after which the particles were collected by centrifugation, washed and resuspended in 50 μl 100% ethanol. The plasmids utilized again included pTα1-RSGFP, pCMV-RSGFP-C1 and pTα1:lacZ. A total of 6–8 μl of the gold-bound DNA suspension was then applied to each sterile macrocarrier disc (Bio-Rad), and the ethanol evaporated. Each carrier was mounted in a Bio-Rad Biolistic particle delivery system, 0.48 cm above the stopping screen; the target samples were placed 6–9 cm from this screen. Helium was pressurized to 1500 psi, and a rupture pressure of 1000–1200 psi was provided by using a 1100 psi rupture disk. Bombardment was performed at a chamber vacuum of 20–25 in Hg, using established protocols (Arnold et al., 1994; Lo et al., 1995). After bombardment, the transfected slurry was then transferred to plates coated with a thin gel composed of 15 μg/ml murine laminin admixed into 10 mg/ml hyaluronic acid (Lev et al., 1994).

3. Adenoviral transfections. Both adult and embryonic VZ cells may be transfected using an adenoviral vector (Bajocchi et al., 1993) into which the gene encoding GFP, under the control of either constitutive (CMV) or neuronal (Tα1) promoters, has been inserted (R. Crystal, Cornell University Medical College, New York, N.Y.). At viral concentrations of 10 pfu/cell, roughly 20% of cultured forebrain cells express GFP 3 days after infection; at 100 pfu/cell, over 30% do so, with this percentage rising to >50% of 1000 pfu/cell.

Immunocytochemistry

Selected plates were fixed in 4% paraformaldehyde, either immediately after FACS, or 3, 5 or 7 days thereafter; they were then immunostained for the neuronal antigen Hu, according to previously described protocols (Barami et al., 1995). Cultures transfected with either pCMV or pTα1-driven lacZ, rather than GFP, were first incubated in Xgal overnight at 4° C. All plates were then immunostained using monoclonal antibody 16A11 (25 μg/ml), which recognizes the neuronal Hu family members HuD, HuC and Hel-N1, all of which are specific to neurons and expressed early in neuronal ontogeny (Szabo et al., 1991; Marusich and Weston, 1992; Marusich et al., 1994; Barami et al., 1995).

$^3$H-thymidine Autoradiography

After Xgal staining first for lacZ/β-galactosidase, and then immunoperoxidase staining for Hu, cultures were autoradiographed as described (Goldman et al., 1992). Briefly, cultures were air-dried from distilled water, and dipped into Kodak NTB-3 emulsion at 46° C. Dipped cultures were exposed at 4° C. for 7 days, then developed using Kodak D-19 at 17° C. for 3 minutes. Developed cultures were observed by using an Olympus IX70 photomicroscope equipped for differential interference contrast.

Flow Cytometry and Sorting

Flow cytometry and sorting of RS-GFP$^+$ cells was performed on a FAC-Star plus, equipped with a V30 management system (Becton-Dickinson, Franklin Lakes, N.J.). Cells (1×10$^6$/ml) were analyzed by light forward and right-angle (side) scatter for RSGFP fluorescence through a 530±30 nm bandpass filter, as they traverse the beam of an argon ion laser (488 nm, 100 mW). The pTα1: lacZ transfected control cells were used to set the background fluorescence. For the test samples transfected with Tα1-RSGFP, any cells having fluorescence higher than background were sorted, at 3000 cells/sec. Sorted cells are plated onto laminin/hyaluronic acid-coated plates into media containing 1- FBS and bFGF (15 ng/ml), at ≧1×10$^5$/ml; these were switched into 10% FBS with 20 ng/ml BDNF 3–4 days after sorting, to encourage neuronal differentiation and survival after initial precursor cell clonal expansion in 1% FBS/bFGF (Kilpatrick and Bartlett, 1995).

The Construction of Tα1-RSGFP pRSGFP-C1, a red-shifted mutant of GFP, was obtained from Clontech Laboratories, Inc. (Palo Alto, Calif.), and pTα1:lacZ, with 1.1 kb of 5' flanking sequence of the Tα1 gene, from Dr. F. Miller (Univ. Toronto). For each, plasmid DNA was transformed into DH-5a cells, and colonies grown on L-broth with 50 mg/ml kanamycin. To construct Tα1-RS/GFP, primers were used to amplify the 5' flanking sequence of the Tα1 gene by PCR: 5': SEQ ID NO:1: 5'-CTTACATATGCTGAATTCCGTATTAG-3 '; 3': SEQ ID NO:2: 5'-GCTCACCGGTGTTGCTGCTTCGCG-3'. To subclone the Tα1 promoter into pRS/GFP-C1, NdeI and AgeI sites were introduced into the 5' and 3' primers; the 1.1 kb PCR product of the Tα1 5' flanking fragment was then inserted into the SmaI site of pbluescript via blunt-end ligation, followed by excision and gel purification of the NdeI-AgeI Tα1 fragment. pRSGFP was digested by AseI and AgeI, and the CMV promoter excised. The remaining pRSGFP was ligated with the NdeI-AgeI Tα1, and the resulting plasmid was designated Tα1-RS/GFP (see FIG. 1).

Figure 2:
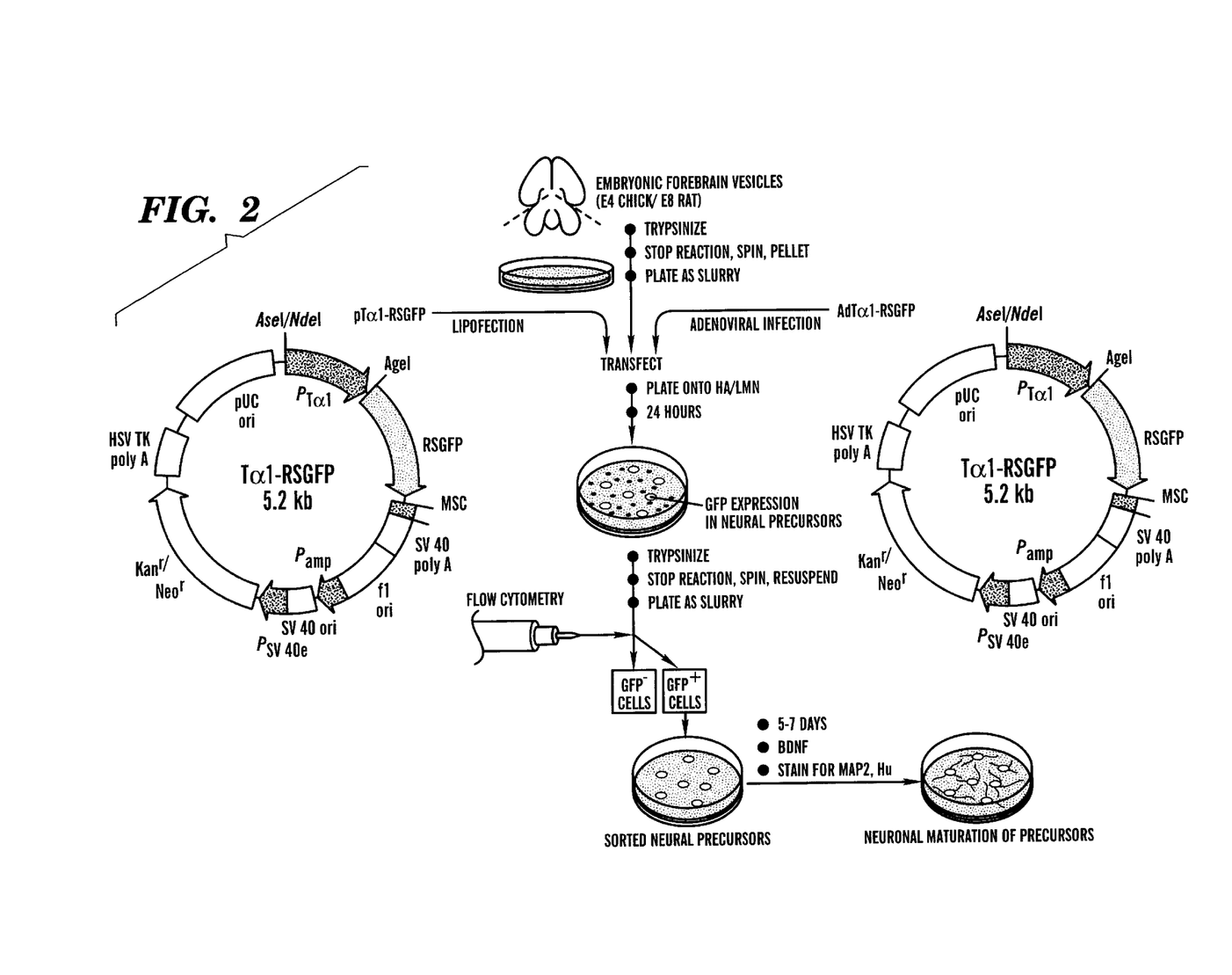
FIG. 2 illustrates the preparation and enrichment of neural precursor cells from the embryonic forebrain.
Figure 3:
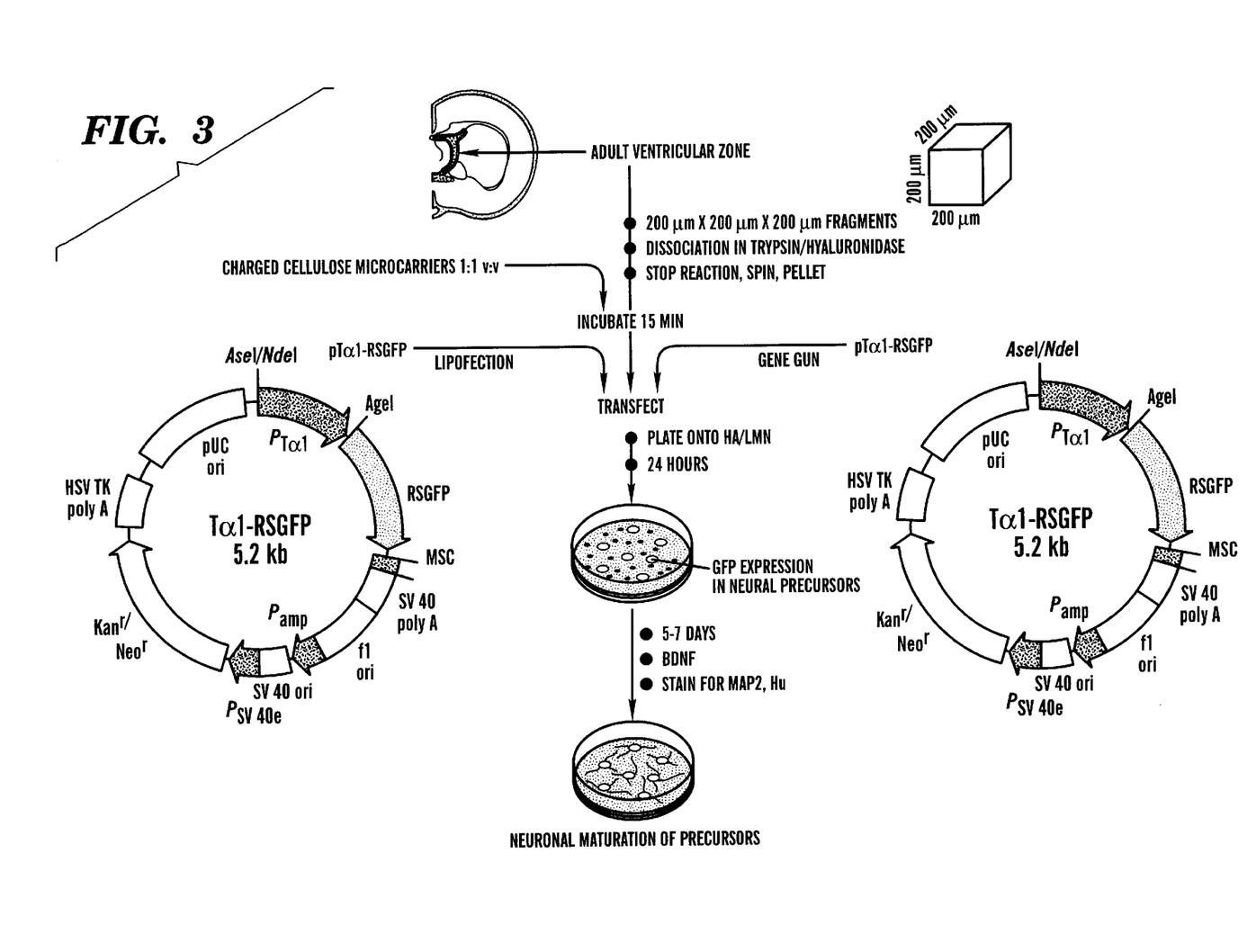
FIG. 3 illustrates the identification of neural precursor cells from the adult ventricular zone, using biolistic and liposomal techniques.
Figure 4:
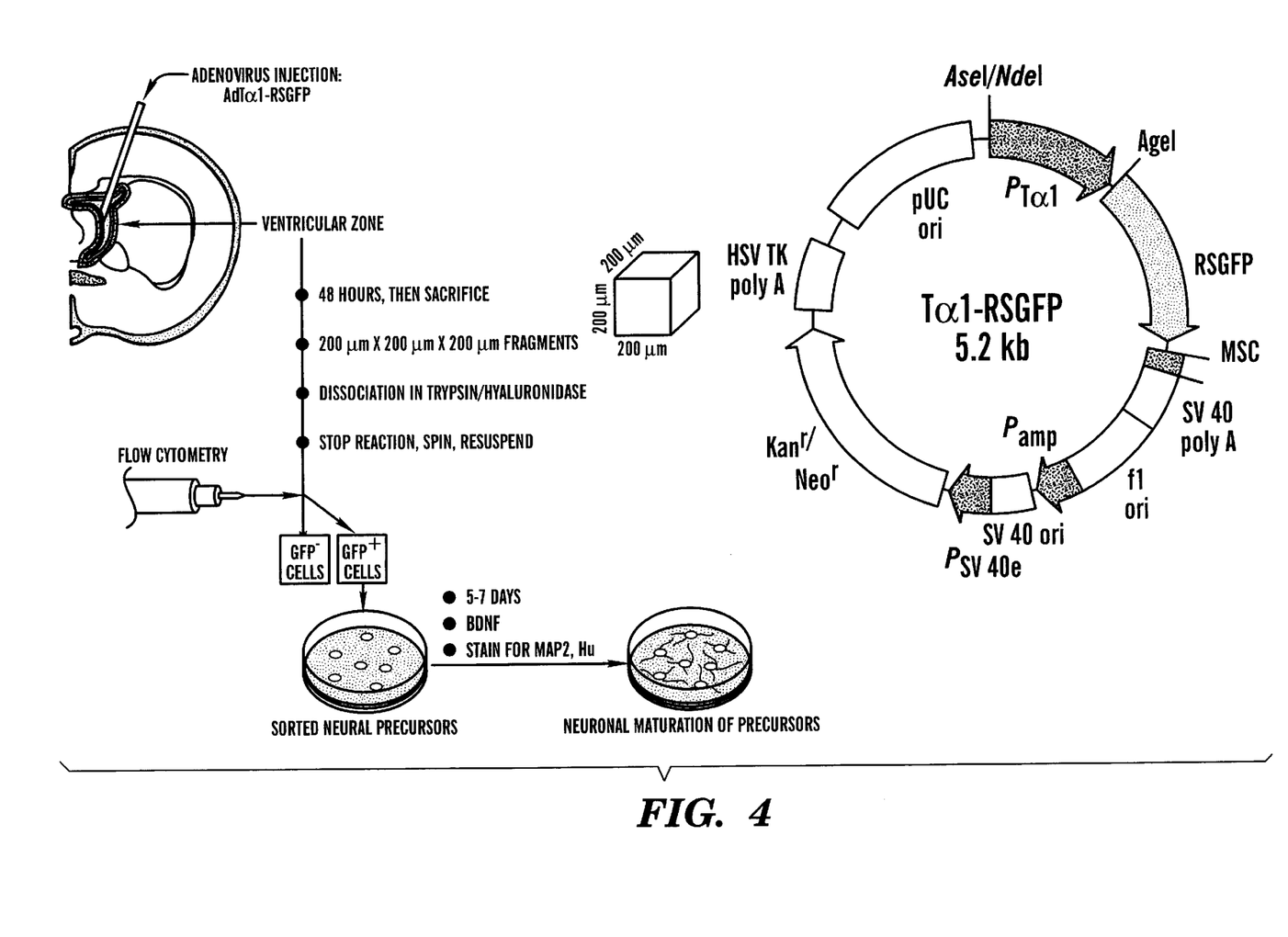
FIG. 4 illustrates the identification and enrichment of neural precursor cells from the adult ventricular zone, using adenoviral delivery of the Tα1-GFP transgene.

The procedure for the preparation and enrichment of neural precursor cells from the embryonic forebrain is shown in FIG. 2. The procedure for the identification of neural precursor cells from the adult ventricular zone using biolistic and liposomal techniques is shown in FIG. 3. The procedure for the identification and enrichment of neural precursor cells from the adult ventricular zone, using adenoviral delivery of the Tα1-GFP transgene is shown in FIG. 4.

Figure 5:
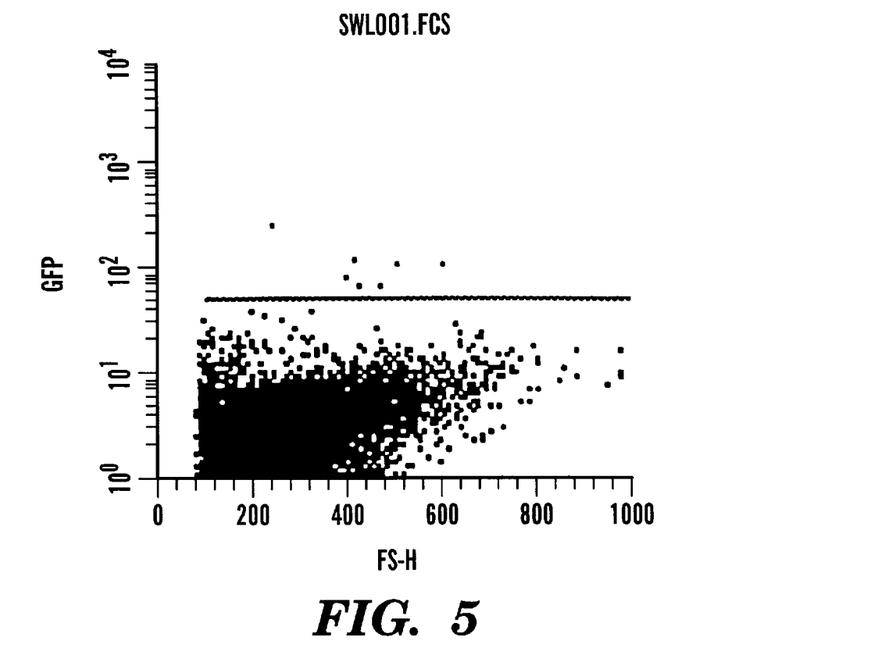
FIG. 5 illustrates GFP fluorescence intensity plotted against forward scatter for control E4 chick forebrain cells transfected with Tα1-lacZ and sorted 36 hr later.
Figure 6:
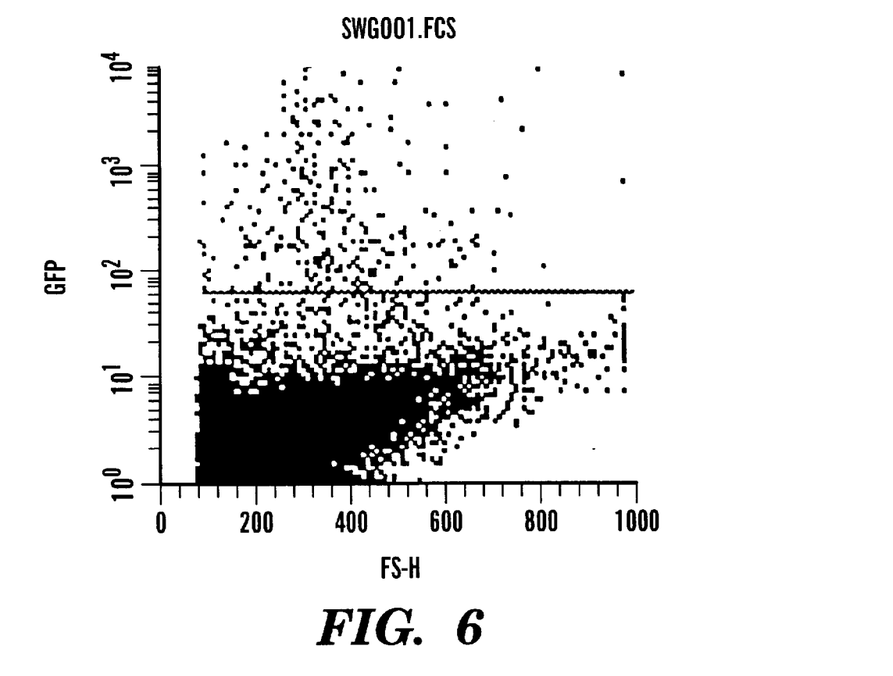
FIG. 6 illustrates GFP fluorescence intensity plotted against forward scatter for a sample of embryonic brain from which neuronal precursor cells were isolated and removed by fluorescence activated cell sorting after transfection with Tα1-RSGFP (right panel), compared to controls transfected with the non-fluorescent Tα1-lacZ control (left panel)

FIGS. 5 and 6 show that neuronal precursors and their neuronal progeny may be separated from a larger brain cell population by FACS, on the basis of neuronal Tα1 tubulin-driven expression of the green fluorescent protein. Each of FIGS. 5 and 6 represent GFP fluorescence intensity plotted against forward scatter, an index of cell size. In FIG. 5, control E4 chick forebrain cells were transfected with Tα1-lacZ and sorted 36 hr later. In FIG. 6, a matched cell pool was separated after transfection with Tα1-RS/GFP. Each FIG. shows 10,000 cells (events). In FIG. 6, 4.2% of the initial pool were separated from the remainder on the basis of their Tα1-expressed GFP. Tα1-driven expression of the transgene indicates that these cells may be neuronally-committed precursors. Tα1-GFP separated cells immediately after sorting, most of which (303/482, or 84% of the cells in 5 sample fields) expressed the early neuronal protein Hu, indicating substantial enrichment of the precursor pool. A day later, GFP expression by flat, undistinguished but probably neuronally-committed cells (Tα1-GFP$^+$/Hu$^+$) was shown. Three days later, one cell developed neuronal morphology with the other remaining morphologically primitive.

Propagation and transfection of adult SVZ-derived neurons in serum-free suspension culture A cluster of new neurons' migrating from a microcarrier-borne aggregate of ventricular zone cells derived from the adult forebrain, 2 weeks in vitro, was seen. This aggregate was raised the first week in suspension culture, during which it was maintained in 1% FBS and 20 ng/ml bFGF. It was then plated onto a hyaluronic acid/laminin gel, in 10% FBS with 20 ng/ml BDNF, and photographed a week later. The neuronal outgrowth from a carrier-borne adult rat SVZ explant after 12 DIV, the first 5 days in serum-free suspension culture, and the latter 7 days after plating onto laminin (after staining for MAP-2), verified the identity of neurons emerging from plated SVZ aggregates. The methods of Lo et al. (1994) were used for particle-mediated delivery to transfect pTα1-RS/GFP into adult SVZ cells in carrier-borne aggregates. Transfectional efficiency and Tα1-driven GFP expression appear analogous in adult avian and mammalian cultures. Successful transfectants were observed a week later, as brightly fluorescent, GFP$^+$ neurons.

EXAMPLE I

The red-shifted green fluorescent protein, when driven by the neural Tα1 promoter, was an effective live cell marker of neuronal phenotype. Until recently, no technique was suitable for identifying live neuronal precursors as such; approaches for precursor identification and lineage analysis, such as nestin immunolocalization and retroviral introduction of reporter genes, have been limited in that immunolabeled and reporter-labeled cells could only be identified after fixation and histochemistry. Clonal relationships could be ascertained, but not division-by-division genealogies and family trees. To follow single cells in real-time requires a heritable non-toxic reporter with detectable expression in live cells. The gene encoding green fluorescent protein (GFP; Chalfie et al., 1994) fulfilled these criteria, and the advent of mutated forms of GFP that emit more strongly than the native protein, together with the development of forms amenable to stable translation in higher vertebrates, have made GFP an effective live cell reporter (Cheng et al., 1996).

Constructs of both neuronal (Tα1 tubulin; Miller et al., 1987; Gloster et al., 1994) (see FIG. 1) and non-neuronal (CMV) promoters driving expression of a red-shifted mutant GFP were developed. As a first step, these constructs were transfected into dissociated cells derived from either E8 rat or E4 chick telencephalic vesicle. At these time points, both chick and rat forebrain anlagen are heavily enriched in premitotic neural precursor cells; most cells are in the VZ, or have just initiated parenchymal migration. These cells were first dissociated into monolayer culture, and 12 hrs after plating, were transfected with either PCMV-RS-GFP or pTα1-RS-GFP, or alternatively, with CMV and Tα1 coupled to lacZ. The Tα1 /hRS-GFP construct is strongly expressed by precursors as well as their neuronal progeny. In both the VZ cell and neuronal transfectants, RS-GFP fluorescence driven by Tα1 quenched little, showed no evidence of toxicity, and remained bright for over a week after transfection.

EXAMPLE II

Tα1-GFP expressing cells developed into neurons in the days following transfection. Embryonic forebrain cultures were first observed for expression of the Tα1 driven hRS-GFP transgene, as a prelude to separating young neurons and their precursors from the larger cell population on the basis of GFP transgene expression. Dispersed cells derived from E8 telencephalic vesicles cells were transfected 6 hrs after being plated into monolayer culture. The location of single GFP$^+$ co-derived cell clusters were assessed at baseline 24 hrs later. The plates were then switched into standard media (DMEM/F12/N2) supplemented with 10% FBS and 20 ng/ml BDNF; they were fixed 2 days later, then immunostained for Hu protein, a neuronal RNA-binding protein (Marusich and Weston, 1992; Barami et al., 1995).

EXAMPLE III

Fluorescence-activated cell sorting based upon Tα1 driven GFP expression allows the enrichment of neuronal precursor cells from the embryonic ventricular zone. Having established the effectiveness of the plasmid construct in driving specific neuronal expression of GFP, this technique was then combined with fluorescence activated cell sorting (FACS) to enrich neuronally-committed VZ cells on the basis of their Tα1-RSGFP expression. Using sequential preparation of VZ cultures, transfection with pTα1-RS-GFP, and cell sorting based upon GFP fluorescence, both embryonic chick and rat brain neural precursors were enriched, in a form which allows their subsequent maturation and function.

EXAMPLE IV

FACS-isolated Tα1-GFP$^+$ cells developed neuronal antigenicity in vitro. In this set of experiments, dispersed E8 telencephalic vesicle cells were transfected 12 hrs after plating in DMEM/F12/N2 supplemented with 5% FES. 36 hrs later, they were removed by trypsin-dissociation, then subjected to FACS. After separation, each GFP-expressing aliquot, averaging $5 \times 10^4$ cells/ml, was distributed into 24-well plates at $1 \times 10^4$ cells/well, then incubated in media containing 10% FES and 20 ng/ml BDNF for 1 week.

Each culture was assessed for the frequency of GFP$^+$ and Hu$^+$ cells, every other day for 6 days after sorting. In this case, the experimental endpoint was the proportion of Hu$^+$ cells within the total sorted population (all nominally GFP$^+$ following sorting), as a function of time after sorting. This value was also compared to that in unsorted controls plated directly.

The number of GFP$^+$/Hu$^+$ cells increased in the first 2 days after sorting under these culture conditions. In contrast to a matched group of unsorted cells, the proportion of Hu$^+$ cells within the sorted population was maintained at over 80% throughout the six day period after sorting. (In matched cultures of E8 forebrain cells, not subjected to sorting, a biphasic rise and fall in the proportion of Hu$^+$ cells was typically noted; in the first 2 to 3 days after plating, both the absolute number and proportion of Hu⁺ cells increased, presumably as a result of precursor division and daughter cell neuronal differentiation, followed thereafter by the progressive dilution of the neuronal pool by proliferating glial cells. This typically resulted in an Hu labeling index of less than 50% after 6 days for unsorted E6 cells, less than 20% at 6 days for E8 cells, and less than 15% at 6 days for E6 forebrain cells.)

EXAMPLE V

Tα1-GFP transfections of adult brain have also been successful, with Tα1-driven RS-GFP expression following both ballistic particle-mediated (Arnold et al., 1994; Lo et al., 1994) and lipofectin transfections of adult rat VZ explants raised on micro-carriers. These charged cellulose microcarriers allowed the serum-free suspension culture of adult VZ precursor cells and aggregates. Dissociation of adult brain tissue is associated with substantial losses in cells, generally over 99% (Reynolds and Weiss, 1992). Explantation improves viability, but at the expense of making transfection more difficult. Organotypic explants severely limit access of both liposomes and viral vectors to their targets. Particle delivered-DNA provides some advantage in this regard, but is highly variable in its transfection efficacy, and the resulting incorporated gold particles effectively preclude later single cell dissociation and FACS. As a result, particle delivery as a means of introducing fluorescent transgenes is, for the purposes herein, effectively limited to cell suspensions and slurries, such as microcarrier-borne adult-explants, for which no subsequent cell separation or sorting is anticipated.

To address the respective shortcomings of both enzymatic dissociation and bulk explantation, a method for the preparation of incompletely dissociated adult VZ precursor cells in suspension culture was developed, which are maintained as small aggregates bound to charged cellulose microcarriers. This method allows the long-term serum-free culture of very small explants of adult brain tissue, whose cells remain viable, and precursors mitotically-competent, for several weeks in suspension. To this end, very small VZ tissue fragments of <0.01 mm³, less than a tenth the volume of previously described organotypic explants (Goldman, 1990; Kirschenbaum and Goldman, 1995), are raised on charged cellulose microcarriers (Shahar, 1990) in serum-free suspension culture. After experimenter-defined periods of mitogenic stimulation and clonal expansion of up to 2 weeks duration, the cell-bearing microcarriers are plated onto a thin gel of hyaluronic acid (Levy et al., 1996) admixed with laminin, which supports the attachment and spread into monolayer culture of those cells generated in suspension. This technique allowed for the maintenance of small aggregates of <20 VZ cells in suspension, with ³H-thymidine-confirmed clonal expansion to added FGF2, for over 2 wks in vitro; the subsequent plating onto the HA/LMN gels allowed the recovery of cells within these aggregates readily and reliably, with a viable yield of >95%. Furthermore, the addition at that point of BDNF (20 ng/ml) allowed maintenance of these expanded numbers of newly generated neurons. This technique, in tandem with newly available cell-specific markers for young, newly committed neurons, such as Hu (Marusich et al., 1994; Barami et al., 1995), allowed for the raising of neural precursors from both adult avian and rat brains, in higher yields than previously achievable.

EXAMPLE VI

Particle-mediated transfection of carrier-bound VZ microexplants yielded Tα1-driven GFP expression by adult VZ cells and their neuronal progeny.

EXAMPLE VII

A strategy for the identification, isolation and enrichment of neural precursors and their neuronal daughter cells, using fluorescence-activated cell sorting of VZ cells transfected with green fluorescent protein (GFP), driven by the neuronal Tα1 tubulin promoter, is provided by the subject invention. By this means, neural precursors and their young neuronal daughters can be identified and harvested from both avian and mammalian forebrain. This approach allows for the enrichment of neural precursors from both adults and embryos, with a yield substantially higher than that achievable through standard techniques of selective dissection and differential centrifugation.

Preparation of precursors from adult human brain. The adult human temporal VZ, like that of birds and rodents, can also generate new neurons in vitro (Kirschenbaum et al., 1994). These neurons can be generated through in vitro mitogenesis, mature functionally in culture, and appear to respond to sequential bFGF and BDNF treatment with clonal expansion and neuronal differentiation and survival, leading to substantially expanded numbers of new neurons from the adult VZ (Pincus et al., 1996). Thus, precursors derived from the adult human VZ may obey many of the same rules as their rodent counterparts, and as such, might also be preparable using neurally-targeted GFP expression and FACS. However, neuronal precursors appear to be more scarce in the adult human VZ than in its infraprimate counterparts. As a result, adenoviral gene delivery with its high transfection efficiencies, may be required for the specific harvest and enrichment of competent neuronal precursors from the adult human ventricular zone.

Concurrent enrichment of multiple progenitor and daughter cell phenotypes. By providing a means of identifying neuronal precursors while alive, even when present in small numbers in mixed populations, the use of fluorescent transgenes driven by cell type-selective promoters such as Tα1 will allow the specification of phenotype to be studied and perturbed on the single cell level, an approach that had previously only been feasible on larger populations. Indeed, when used in conjunction with post-transfection FACS, this strategy may permit the enrichment of any cell type for which stage- or phenotype-specific promoters are available. For instance, similar GFP constructs based upon early oligodendrocyte promoters, such as CNPase or JC virus, might similarly permit the enrichment of oligodendrocytic as well as neuronal precursors from the VZ. As a result, spectrally distinct GFP variants with non-overlapping emission spectra (Heim and Tsien, 1996), each driven by a different cell-specific promoter, will allow concurrent identification of neuronal and oligodendrocytic precursors in vitro. Multi-channel cell sorting based upon the concurrent use of several lasers with non-overlapping excitation lines, such as Ar—K and He—Ne, should then allow the separation and simultaneous isolation of several distinct precursor phenotypes from a given brain sample.

Enrichment of progenitors and their progeny from non-brain tissues. Furthermore, this technique should be extendable to any cell types for which cell-specific promoters are or become available. For example, endothelial cells might be separated on the basis of the Factor VIII promoter, bone marrow stem cells by virtue of the promoter for CD34, etc.

Overview By providing a means to identify and enrich viable neural precursor cells, from adult as well as fetal brain, this strategy may allow a significant acceleration in the study of precursor and stem cell biology. In particular, it may allow the preparation and enrichment of neural precursor cells in sufficient number as to permit implantation and engraftment studies to proceed using native, unpassaged adult-derived progenitor cells. This approach may spur the development of induced adult neurogenesis as a viable therapeutic modality for the structural repair of the damaged central nervous system, whether in the brain or spinal cord.

Although preferred embodiments have been depicted and described in detail herein, it will be apparent to those skilled in the relevant art that various modifications, additions, substitutions and the like can be made without departing from the spirit of the invention and these are therefore considered to be within the scope of the invention as defined in the claims which follow.

LIST OF REFERENCES CITED

Alouani et al., Hum Gene Ther 3:487–499 (1992).
Andersen et al., Eur J Cell Bio 62:324–332 (1993).
Arnold, D., et al., Proc Natl Acad Sci USA 91:9970–9974 (1994).
Barami, K., et al., Neuron 13:567–582 (1994).
Barami, K., et al., J Neurobiol 28:82–101 (1995).
Birse, S., et al., J Comp Neurol 194:291–301 (1980).
Cambi and Kamholz, Neurochem Res 19:1055–1060 (1994).
Chalepakis et al., DNA Cell Biol 13:891–900 (1994).
Chalfie, M., et al., Science 263:802–805 (1994).
Cheng, L., et al., Nature Biotech 14:606–609 (1996).
Chin et al., J Biol Chem 269:18507–18513 (1994).
Ching et al., J Biol Chem 266:19459–19468 (1991).
Drago, J., et al., Proc Natl Acad Sci USA 88:2199–2203 (1991).
Gage, F., et al., Ann Rev Neurosci 18:159–192 (1995a).
Gage, F., et al., Proc Natl Acad Sci USA 92:11879–11883 (1995b).
Gloster, A., et al., J Neurosci 14:7319–7330 (1994).
Goldman, S., J Neurosci 10:2931–2939 (1990).
Goldman, S., The Neuroscientist 1:338–350 (1995).
Goldman, S., In: *Isolation, characterization and utilization of CNS stem cells*. F. Gage, Y. Christen, eds., Foundation IPSEN Symposia. Springer-Verland, Berlin, p. 43–65 (1997).
Goldman, S., et al., Glia 8:150–160 (1993).
Goldman, S., and Kirschenbaum, B., Soc Neurosci Abstr 317.7 (1995).
Goldman, S., and Nedergaard, M., Dev Brain Res 68:217–223 (1992).
Goldman, S., and Nottebohm, F., Proc Natl Acad Sci USA 80:2390–2394 (1983).
Goldman, S., et al., *J Cereb Blood Flow Metab* 9:471–477 (1989).
Goldman, S., et al., Molec Cell Neurosci 7:29–45 (1996).
Goldman, S., et al., J Neuroscience 12:2532–2541 (1992).
Gritti, A., et al., J Neurosci 16:1091–1100 (1996).
Heim, R., and Tsien, R., Current biology 6:178–183 (1996).
Hidalgo, A., et al., J Neurobiol 27:470–487 (1995).
Holst et al., J Biol Chem 269:22245–22252 (1994).
Kaplan, M., and Hinds, J., Science 197:1092–1094 (1977).
Karpov et al., Biol Cell 76:43–48 (1992).
Kilpatrick, T., and Bartlett, P., J Neurosci 15:3563–3661 (1995).
Kirschenbaum, B., et al., Cerebral Cortex 4:576–589 (1994).
Kirschenbaum, B., and Goldman, S., Soc Neurosci Abstr 317.8 (1995b).
Kirschenbaum, B., and Goldman, S., Proc Natl Acad Sci USA 92:210–214 (1995a).
Koh, J., et al., Science 268:573–575 (1995).
Korr, H., Adv Anat Embryol Cell Biol 61:1–72 (1980).
Krebs et al., J Virol 69:2434–2442 (1995).
Le Van Thai et al., Mol Brain Res 17:227–238 (1993).
Levy, A., et al., J Neurosci Res 43:719–725 (1996a).
Levy, J., et al., Nature Biotechnol 14:610–614 (1996b).
Liu and Fischer, Gene 171:307–308 (1996).
Lo, D., et al., Neuron 13:1263–1268 (1994).
Lois, C., and Alvarez-Buylla, A., Proc Natl Acad Sci USA 90:2074–2077 (1993).
Marusich, M., and Weston, j., J Dev Biol 149:295–306 (1992).
Marusich, M., et al., J Neurobiol 25:143–155 (1994).
Mercer et al., Neuron 7:703–716 (1991).
Miller, F., et al., J Cell Biol 105:3065–3073 (1987).
Miller, F., et al., J Neurosci 9:1452–1463 (1989).
Morshead, C., et al., Neuron 13:1071–1082 (1994).
Nedergaard, M., et al., J Neurosci 11:2489–2497 (1991).
Morshead, C., and van der Kooy, D., J Neurosci 12:249–256 (1992).
Palmer, T., et al., Mol Cell Neurosci 6:474–486 (1995).
Pincus, D., et al., Ann Neurology 40:550 (1996).
Rasika, S., et al., Proc Natl Acad Sci USA 91:7854–7858 (1994).
Reynolds, B., and Weiss, S., Science 255:1707–1710 (1992).
Richards, L., et al., Proc Natl Acad Sci USA 89:8591–8595 (1992).
Sambrook et al., *Molecular Cloning: A Laboratory Manual*, 2d Edition, Cold Spring Harbor Laboratory Press, Cold Spring Harbor, N.Y. (1989).
Scherer et al., Neuron 12:13G3–1375 (1994).
Shah, N., et al., Cell 85:331–343 (1996).
Shahar, A., In: *Methods in Neurosci*, vol. 2.: *Cell Culture*, M. Conn, ed., Academic Press, San Diego, p. 195–209 (1990).
Starr et al., Brain Res 638:211–220 (1994).
Sturrock, R., *Adv Cell Neurobiol*, vol. 3, Academic Press, New York, p. 1–33 (1982).
Szabo, A., et al., Cell 67:325–333 (1991).
Takebayashi et al., J Biol Chem 270:1342–1349 (1995).
Vescovi, A., et al., Neuron 11:951–966 (1993).
Wrabetz et al., J Neurosci Res 36:455–471 (1993).

What is claimed is:

1. An in vitro method of identifying and separating a single mammalian neural cell type or a progenitor thereof from a mixed population in tissue containing other mammalian brain or spinal cord cell types, wherein the single mammalian neural cell type or progenitor thereof is either a neuronal progenitor cell, an oligodendrocyte progenitor cell, a neuron, or an oligodendrocyte, said method comprising:

selecting a promoter which functions only in said single neural cell type or a progenitor thereof and not in the other cell types;

introducing a nucleic acid molecule encoding a marker protein under control of said promoter into all cell types of said mixed population in tissue containing other mammalian brain or spinal cord cell types;

allowing only the single neural cell type or a progenitor thereof, but not the other cell types, within said mixed population to express said marker protein;

identifying cells of said mixed population of cell types that are expressing the marker protein, which are restricted to the single neural cell type or progenitor thereof, and separating the cells expressing the marker protein from said mixed population, wherein said separated cells are restricted to said single neural cell type or a progenitor thereof.

2. The method of claim 1, wherein said introducing comprises viral mediated transformation of all cell types of said mixed population in tissue containing other mammalian brain or spinal cord cell types.

3. The method of claim 2, wherein said viral mediated transformation comprises adenovirus mediated transformation.

4. The method of claim 1, wherein said introducing comprises electroporation.

5. The method of claim 1, wherein said introducing comprises liposomal mediated transformation of all cell types of said mixed population in tissue containing other mammalian brain or spinal cord cell types.

6. The method of claim 1, wherein said promoter is selected from the group consisting of:
a neuron-specific enolase promoter;
a MAP-1B promoter;
an L1 promoter;
an aromatic amino acid decarboxylase promoter;
a dopamine β-hydroxylase promoter;
an NCAM promoter;
an HES-5 HLH protein promoter;
an α1-tubulin promoter;
an α-internexin promoter;
a peripherin promoter;
a synapsin promoter; and
a GAP-43 promoter.

7. The method of claim 1, wherein said promoter is selected from the group consisting of:
a cyclic nucleotide phosphorylase I promoter;
a myelin basic protein promoter;
a JC virus minimal core promoter;
a proteolipid protein promoter; and
a cyclic nucleotide phosphorylase II promoter.

8. The method of claim 1, wherein the tissue is brain tissue.

9. The method of claim 1, wherein the tissue is spinal cord tissue.

10. The method of claim 1, wherein the neural cell type or progenitor thereof is a neuronal cell type or progenitor thereof.

11. The method of claim 1, wherein the neural cell type or progenitor thereof is an oligodendrocyte or progenitor thereof.

12. The method of claim 1, wherein the neural cell type or progenitor thereof is human.

13. A method according to claim 1, wherein the neural cell type or progenitor thereof is a single neural cell type.

14. A method according to claim 1, wherein the neural cell type or progenitor thereof is a progenitor of a single neural cell type.

15. The method according to claim 1, wherein the marker protein is a fluorescent protein and the cells that are expressing the marker protein are fluorescent.

16. The method of claim 15, wherein said separating comprises fluorescence activated cell sorting.

17. The method according to claim 15, wherein the marker protein is a fluorescent protein and the cells that are expressing the marker protein are fluorescent.

18. An in vitro method of identifying and separating a progenitor of a single mammalian cell type from a mixed population containing other mammalian cell types, said method comprising:

selecting a promoter which functions only in said progenitor of a single cell type and not in the other cell types;

introducing a nucleic acid molecule encoding a marker protein under control of said promoter into all cell types of said mixed population;

allowing only the progenitor of a single cell type, but not the other cell types, within said mixed population to express said marker protein;

identifying cells of said mixed population of cell types that are expressing the marker protein, which are restricted to the progenitor of a single cell type; and separating the cells that are expressing the marker protein from said mixed population, wherein said separated cells are restricted to said progenitor of a single cell type.

19. The method of claim 18, wherein said introducing comprises viral mediated transformation of all cell types of said mixed population in tissue containing other mammalian brain or spinal cord cell types.

20. The method of claim 19, wherein said viral mediated transformation comprises adenovirus mediated transformation.

21. The method of claim 20, wherein said introducing comprises electroporation.

22. The method of claim 18, wherein said introducing comprises liposomal mediated transformation of all cell types of said mixed population in tissue containing other mammalian brain or spinal cord cell types.

23. The method of claim 18, wherein the progenitor of a single mammalian cell type is from a human.

24. An in vitro method of identifying and separating progenitors of a single mammalian neural cell type and differentiating the progenitors into their respective mature forms, said method comprising:

providing a progenitor of a single mammalian neural cell type in a mixed population in tissue containing other mammalian brain or spinal cord cell types, wherein the progenitor is either a neuronal cell progenitor or an oligodendrocyte progenitor;

selecting a promoter which functions only in said progenitor of the single neural cell type and not in the other cell types;

introducing a nucleic acid molecule encoding a marker protein under control of said promoter into all cell types of said mixed population;

allowing only the progenitors of the single neural cell type, but not the other cell types, within said mixed population to express said marker protein;

identifying cells of said mixed population of cell types that are expressing the marker protein, which are restricted to the progenitors of the single neural cell type;

separating the cells that are expressing the marker protein from said mixed population, wherein said separated cells are restricted to the progenitors of said single neural cell type; and differentiating the separated progenitors of said single neural cell type into cells of the single neural cell type.

25. The method according to claim 24, wherein the marker protein is a fluorescent protein and the cells that are expressing the marker protein are fluorescent.

26. An in vitro method of identifying and separating progenitors of a single mammalian cell type and differentiating the progenitors into their respective mature forms, said method comprising:

providing a progenitor of a single mammalian cell type in a mixed population containing other mammalian cell types;

selecting a promoter which functions only in said progenitor of the single cell type and not in the other cell types;

introducing a nucleic acid molecule encoding a marker protein under control of said promoter into all cell types of said mixed population;

allowing only the progenitors of the single cell type, but not the other cell types, within said mixed population to express said marker protein;

identifying cells of said mixed population of cell types that are expressing the marker protein, which are restricted to the progenitors of the single cell type;

separating the cells expressing the marker protein from said mixed population, wherein said separated cells are restricted to the progenitors of said single cell type; and differentiating the separated progenitors of said single cell type into cells of the single cell type.

27. The method according to claim 26, wherein the marker protein is a fluorescent protein and the cells that are expressing the marker protein are fluorescent.

28. The method of claim 27, wherein said separating comprises fluorescence activated cell sorting.

* * * * *